United States Patent [19]
Silva et al.
[11] Patent Number: 4,994,594
[45] Date of Patent: Feb. 19, 1991

[54] OLIGOMERIC CARBONATE CHAINSTOPPERS

[75] Inventors: James M. Silva, Clifton Park, N.Y.; Robert A. Pyles, Bethel Park, Pa.
[73] Assignee: General Electric Company, Schenectady, N.Y.

[21] Appl. No.: 161,689
[22] Filed: Feb. 29, 1988
[51] Int. Cl.[5] .............. C07C 69/96
[52] U.S. Cl. .............. 558/268; 252/182.31; 528/196; 528/199; 528/202; 528/203; 528/204; 528/371; 528/372; 558/269; 558/271; 558/272; 558/274
[58] Field of Search .............. 558/268, 271, 274, 272, 558/269

[56] References Cited

U.S. PATENT DOCUMENTS 3,028,365 4/1962 Schnell et al. .............. 528/196
3,549,682 12/1970 Vernaleken .............. 558/274
4,089,888 5/1978 Tokumitsu et al. .............. 558/268
4,122,112 10/1978 Koda et al. .............. 558/268
4,247,475 1/1981 Ching .............. 260/465 D
4,616,077 10/1986 Silva .............. 528/371
4,638,077 1/1987 Brunelle et al. .............. 558/281
4,701,544 10/1987 Silva .............. 558/281

FOREIGN PATENT DOCUMENTS 8602363 9/1986 Netherlands .

*Primary Examiner*—Vivian Garner
*Attorney, Agent, or Firm*—William H. Pittman; James C. Davis, Jr.

[57] ABSTRACT

Oligomeric carbonate dihydroxyaromatic-based chainstoppers are disclosed. One example of this type of chainstopper is a bisphenol A bischloroformate oligomer monocapped with phenol. These chainstoppers may be prepared by phosgenating a dihydroxyaromatic compound to terminate one or both of the terminal oxygen atoms with chlorocarbonyl groups, followed by reaction of the chlorocarbonyl-terminated material with a phenolic-type compound in the presence of an amine catalyst. The chainstoppers of the present invention are very useful in accurately controlling the molecular weight of polycarbonates formed by various processes, while also preventing the formation of undesirable by-products, such as diarylcarbonates.

3 Claims, No Drawings

OLIGOMERIC CARBONATE CHAINSTOPPERS

This invention relates generally to polymerization control by the use of chainstoppers, and more particularly to improved oligomeric chainstopper compositions which are particularly effective during polymerization of polycarbonates.

The use of chainstoppers during polymerization reactions is known in the art. They are also frequently referred to as endcappers, chain terminators, molecular weight regulators, and various other terms. Regardless of name, they generally perform one function, as described in U.S. Pat. No. 3,028,365, issued to Schnell et al.: regulation of molecular weight via termination of the polymer chain at a desired chain length.

Phenols and structurally-related materials such as tertiary-butylphenol and cyclohexylphenol are illustrative monofunctional compounds which often serve as chainstoppers during the preparation of polycarbonates by interfacial techniques. While these materials are generally effective for molecular weight control, their use has several disadvantages. One major drawback associated with phenol-type chainstoppers is the tendency for side reaction between the chainstopper and the phosgene added to the reaction mixture. In addition to disturbing the preselected stoichiometry of the polymer synthesis, this side reaction results in the formation of diaryl carbonates, which are undesirable by-products for several reasons.

The presence of diaryl carbonates such as diphenylcarbonate in the polycarbonate product often causes difficulties in subsequent molding operations, even when these by-products appear at levels less than 1000 ppm. One of the difficulties involved is "plate-out", i.e., the condensation of diarylcarbonate material on relatively cool areas of the mold. There are also problems when parts are produced using rapid cycle times. In general, it becomes difficult to make parts which are free of physically or optically flawed surfaces.

Furthermore, since the diaryl carbonates are often the last components in a polycarbonate product to solidify, they delay the overall hardening of the product, thereby adversely affecting subsequent operations which require a fully cured material, such as blow molding.

Chainstoppers designed to minimize the presence of diaryl carbonates have been disclosed. For example, Ser. No. 098,170, filed Sept. 18, 1987, now U.S. Pat. No. 4,864,011, on behalf of J. Bussink et al., teaches the use of phenylchloroformate-type compounds as chainstoppers in polycarbonate polymerization. While the phenylchloroformates reduce diaryl carbonate formation, conditions for their use must be very carefully controlled. Furthermore, their use creates other problems as well. For example, these materials can be expensive, as well as being hazardous to ship because of the presence of residual phosgene. Moreover, the phenylchloroformates are susceptible to hydrolysis during polymerization, resulting in the production of phenol, which can react with phosgene to yield the undesirable diaryl carbonate by-products discussed above. These undesirable reactions deplete the supply of chainstopper, thus adversely affecting the control of molecular weight.

It is therefore an object of the present invention to provide a chainstopper compound which is effective in controlling the molecular weight of polycarbonates prepared by various processes, while substantially eliminating the formation of diaryl carbonate by-products.

It is a further object to provide a method for making such a chainstopper.

It is still another object of the present invention to provide a convenient method for preparing polycarbonates of closely-controlled molecular weight which are substantially free from diaryl carbonate by-products.

SUMMARY OF THE INVENTION

The chainstopper of the present invention is useful in controlling the molecular weight of polycarbonate prepared by an interfacial phosgenation process or by the condensation of oligomeric carbonate chloroformates, and has the formula

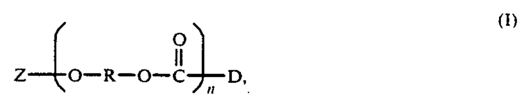

wherein R is at least one divalent aromatic group; Z is either $$-\overset{O}{\overset{\|}{C}}-Cl$$

or hydrogen; D is a monofunctional aromatic group; and n is an integer from 1 to about 10. R is generally the backbone unit of a dihydroxyaromatic compound such as bisphenol A, while D is typically phenol.

The chainstopper may be prepared by phosgenating a dihydroxyaromatic compound within an aqueous/organic mixture to terminate the compound with a chlorocarbonyl group. The resulting material may then be reacted with a phenolic-type group in the presence of an amine catalyst to form the oligomeric chainstopper product.

A method for preparing aromatic polycarbonates is also within the scope of the present invention. A key feature in this method is the use of the chainstopper described above, which results in precise control of polycarbonate molecular weight while also resulting in an unexpected reduction in the level of undesirable by-products, such as diaryl carbonates.

DETAILED DESCRIPTION OF THE INVENTION

The chainstopper of this invention has the formula

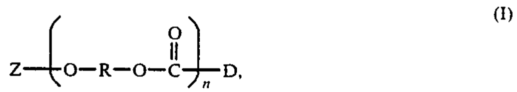

wherein R is at least one divalent aromatic group; Z is either $$\overset{O}{\overset{\|}{C}}-Cl$$

or hydrogen; D is a monofunctional aromatic group; and n is an integer from 1 to about 10. The R values may be aromatic hydrocarbon or substituted aromatic hydrocarbon groups. Exemplary substituents include alkyl, cycloalkyl, alkenyl, halo, nitro, and alkoxy.

Descriptions of suitable divalent aromatic R groups are given in J. Silva's U.S. Pat. Nos. 4,616,077 and 4,701,544, both incorporated herein by reference.

The preferred R values have the formula $$-A^1-Y-A^2- \quad \text{II}$$

wherein each of $A^1$ and $A^2$ is a divalent aromatic group, and Y is a bridging group. The free valence bonds of $A^1$ and $A^2$ usually bond in positions meta or para, relative to Y.

Illustrative values for $A^1$ and $A^2$ are unsubstituted phenylene groups or substituted derivatives thereof, exemplary substituents being alkyl, alkenyl, halo, nitro, alkoxy and the like. Unsubstituted phenylene groups are preferred. In preferred embodiments, both $A^1$ and $A^2$ are p-phenylene, although one or both might alternatively be either o- and/or m-phenylene.

The bridging group, Y, contains one or two atoms which separate $A^1$ from $A^2$. It is usually a hydrocarbon group and particularly, a saturated group such as methylene, cyclohexylmethylene, isopropylidene, and the like, as described in U.S. Pat. No. 4,616,077.

Because of availability and particular suitability for this invention, the preferred group for formula II is a 2,2-bis(4-phenylene) propane radical, which is derived from bisphenol A, with Y being isopropylidene and $A^1$ and $A^2$ each being p-phenylene.

Those of ordinary skill in the art of chemical synthesis realize that the divalent aromatic group R may in fact comprise a mixture of various divalent aromatic groups designed to provide particular characteristics for specific end uses. For example, R may comprise radicals of both bisphenol A and 2,2-bis(3,5-dibromo-4-hydroxyphenyl) propane in various proportions when some degree of fire retardancy is desired for an end product prepared by the use of this chainstopper.

As shown above, chainstoppers of the present invention are terminated at one end with group D, a monofunctional aromatic compound having the formula (III)

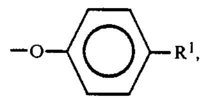

wherein $R^1$ is selected from the group consisting of hydrogen, branched- or straight-chain alkyl groups containing up to about 15 carbon atoms, and aromatic or aliphatic heterocyclic groups containing carbon atoms and at least one other atom selected from the group consisting of oxygen, nitrogen, and sulfur. Exemplary values for $R^1$ include methyl, ethyl, t-butyl, octyl, cumyl, and the like. In preferred embodiments, $R^1$ is hydrogen, i.e., group D is a phenol radical. For the sake of brevity, group D will sometimes be referred to herein as simply the "phenolic group" or "phenolic compound", with the intent that these terms embrace all the compounds of formula III.

In view of overall capping effectiveness and material cost, it is preferred that the number of repeating units (n) be in the range of about 1 to 5.

The term "oligomeric phenylcarbonate bisphenol A chloroformate" as used herein describes one or more chainstoppers of this invention, wherein Z is $$-\overset{\overset{\large O}{\|}}{C}-Cl,$$

R is the 2,2'-bis(phenyl) propane radical of bisphenol A, D is a phenol radical, and at least about 80of the repeating units are in oligomers wherein n is 1–5. These are usually the compounds of choice for use during polycarbonate preparation according to this invention.

The chainstopper of formula I may be prepared by first phosgenating at least one compound containing the chemical structure $$-O-A^1-Y-A^2-O- \quad \text{(IV)}$$

within an aqueous/organic mixture, $A^1$, Y, and $A^2$ being defined above. The phosgenation step serves to terminate one or both of the terminal oxygen atoms with chlorocarbonyl groups, and is usually effected by bubbling phosgene into the reaction mixture which itself is maintained at a pH of about 2 to 11. Reaction temperatures may range from about 0–50° C, while the duration of the reaction usually ranges from a few seconds to about 30 minutes. When a monomerdominated product mixture is desired (as further discussed below), phosgenation is preferably carried out at temperatures of 25° C. or less, and at a pH of about 3–5. Furthermore, the reaction time is shortened, e.g., to 20 minutes or less.

Termination of only one of the terminal oxygen atoms with a chlorocarbonyl group $$-\overset{\overset{\large O}{\|}}{C}-Cl$$

results in the Z group in formula I being hydrogen, i.e., a hydroxy group attached to R. For example, a monochloroformate of the formula (V)

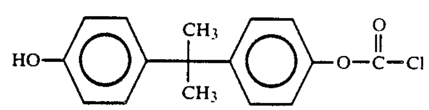

could be reacted with phenol and an alkali metal hydroxide to form the desired hydroxy-terminated chainstopper.

In similar fashion, termination of both terminal oxygen atoms with chlorocarbonyl groups may be carried out. For example, bisphenol A could be reacted with phosgene to prepare a mixture of oligomeric carbonate bischloroformates. Those of ordinary skill are aware of phosgenation levels and other conditions suitable for formation of the chloroformate groups. U.S. Pat. No. 4,638,077, issued to Brunelle et al. and incorporated herein by reference, provides a teaching as to this type of phosgenation reaction, as does the above-referenced U.S. Pat. No. 4,616,077.

The organic component of the mixture is a substantially non-polar organic liquid which forms a two-phase system with water. Illustrative liquids of this type are aromatic hydrocarbons such as toluene and xylene; substituted aromatic hydrocarbons such as chlorobenzene, o-dichlorobenzene and nitrobenzene; chlorinated aliphatic hydrocarbons such as chloroform and methylene chloride; and mixtures of the foregoing with ethers such as tetrahydrofuran. Methylene chloride is generally preferred.

The volume ratio of aqueous to organic phase is not critical to this process, and depends on several factors, such as the particular solvent employed and the concentrations of materials used. Usually, the volume ratio at the conclusion of phosgenation is in the range of about 0.2:1.0 to about 2:1.0 aqueous/organic, respectively.

After phosgenation is deemed complete, the aqueous phase is removed from the reaction mixture by well-known techniques, such as decantation. The chlorocarbonyl-terminated material in the organic phase is then reacted with phenolic compound D. The reaction is carried out in the presence of a basic reagent which functions as a catalyst and acid acceptor. Preferred reagents of this type are aliphatic or heterocyclic tertiary amines which are soluble in the organic phase. Some of these amines are described in U.S. Pat. Nos. 4,617,077, 4,217,438, and 4,368,315, the two last-mentioned references also being incorporated herein by reference. These amines are also described in two pending applications, Ser. Nos. 917,751 and 046,768, filed Oct. 10, 1986 and May 7, 1987, respectively, now U.S. Pat. Nos. 4,737,573 and 4,743,676, respectively, the contents of each being incorporated herein by reference. Illustrative aliphatic amines are triethylamine, tri-n-propylamine, and diethyl-n-propylamine. Illustrative heterocyclic amines include 4-dimethylaminopyridine. Tri-n-alkylamines in which the alkyl groups contain up to about 4 carbon atoms are preferred. In terms of cost, availability, and effectiveness, triethylamine is the most preferred amine catalyst. Effective amounts of the amine are usually in the range of about 0.05–1.0 mole per mole of divalent aromatic group R.

Generally, about 0.01 mole to about 1.0 mole phenolic compound D per mole of divalent aromatic compound is used to form the chainstopper, the objective being to cap one chlorocarbonyl site per molecule of oligomer with the phenolic group.

Reaction between the chlorocarbonyl-terminated material and the phenolic compound D is allowed to proceed for a period of time sufficient to consume substantially all of the phenolic compound. Normally, about 1–60 minutes is required for such a reaction, although various other factors influence reaction time, such as the amount of agitation and the type and level of catalyst/acid acceptor present.

Reaction temperature is generally not a critical parameter in formation of the chainstopper. A suitable temperature range is from about 20° C. to about 100° C, although temperatures outside of this range are also possible. However, temperatures below about 20° C. often do not permit high reaction rates, while temperatures above 100° C. do not provide any special advantages and consume large amounts of energy. A temperature within the range of about 25° C. to about 55° C. is generally appropriate, although higher temperatures may be used if the reaction is to be conducted at elevated pressures.

Another factor affecting reaction temperature is the choice of organic solvents. This factor is of some significance when a continuous-flow stirred tank reactor (further described below) is employed. For example, the use of lower boiling solvents such as methylene chloride may result in a sharp increase in the volume of vapor in the reaction system as reaction temperatures approach the boiling point. The presence of large amounts of vapor decreases the liquid volume in the reaction vessel and may lead to inefficiencies in the overall process.

The chainstopper product may be recovered from the reaction system by methods which are known in the art. For example, the reaction mixture may be quenched with an excess of water or, more preferably, an aqueous acid solution, followed by extraction of any amine-based by-products which are present. An exemplary aqueous acid solution is 3N aqueous hydrochloric acid.

The chainstopper of the present invention may be prepared by the use of a continuous-flow stirred tank reactor (referred to as "CSTR"), details of which are provided in U.S. Pat. No. 4,616,077. In summary, CSTR provides a means for a continuous production operation, and involves conventional reactant introduction means, agitation means, and heating and/or cooling means. The outlet port for the continuous removal of product is typically located on the perimeter of the reactor, at a distance from the bottom sufficient to provide the desired liquid holdup and residence time in the reactor.

Preparation of the chainstopper as described above results in a solution which contains a mixture of oligomers having formula I, i.e., each having a different value of n. In preferred embodiments, at least about 50% of the repeating units should be monomers, i.e., $n=1$. On a commercial scale, use of this chainstopper solution is usually more convenient than, and as effective as, isolation and use of any one oligomer contained therein. For the sake of simplicity, "chainstopper" as used herein refers to either one oligomer or to a mixture of oligomers conforming to formula I, unless otherwise indicated.

The chainstopper may be used in solution, or may be isolated and stored for later use. As mentioned above, a major use is in the preparation of aromatic polycarbonates. For example, the chainstopper might find use in polycarbonate preparation by the interfacial reaction of phosgene with a dihydroxyaromatic compound, or by the condensation of oligomeric carbonate chloroformates. Each of these types of polycarbonate synthesis are well-known in the art and need not be described in detail here. For example, the interfacial method is generally discussed in *Organic Polymer Chemistry.* by K. J. Saunders, Chapman & Hall (1973), pages 240–242. The preparation of bischloroformate compositions and their subsequent conversion to linear polycarbonates is described, for example, in U.S. Pat. Nos. 3,646,102, 4,089,888 and 4,122,112, each incorporated herein by reference; and in the above-mentioned applications designated as Ser. Nos. 917,751 and 046,768.

In general, the chainstopper of the present invention is employed in the same manner as the conventional chainstoppers used in some of the above references, e.g., the monohydroxyaromatic compounds in application Ser. No. 917,751. The amount of chainstopper used depends on several factors, such as the particular groups forming the chain-stopper (within the scope of formula I above), and the molecular weight and weight distribution desired for the polycarbonate product. Those of ordinary skill in the art are aware of these factors and can therefore adjust the chainstopper level according to desired objectives. The examples which follow also illustrate such adjustment. In general, the amount of chainstopper is about 0.5 mole percent to about 10 mole percent based on moles of divalent aromatic groups present in the reaction mixture, excluding that which is present in the chainstopper itself.

An example of polycarbonate preparation by the interfacial process is the catalyzed interfacial reaction of phosgene with at least one divalent aromatic compound in an aqueous/organic medium, and in the presence of an amount of the chainstopper of the present invention which is effective to terminate polymerization at a desired molecular weight for the polycarbonate. The divalent aromatic compound is usually a dihydroxyaromatic compound such as those which form the backbone of the chainstopper. Again, it should be understood that more than one dihydroxyaromatic compound may be used in the reaction, e.g., a combination of bisphenol A with 2,2'-bis(4-hydroxy-3,5-dimethylphenyl) propane and/or with 2,2-bis(3,5-dibromo-4-hydroxyphenyl) propane. The dihydroxyaromatic compounds have the formula $$HO—A^1—Y—A^2—OH$$

wherein $A^1$, $A^2$, and Y are as described above. Typically, about 1.0 to about 3.0 moles of phosgene are employed per mole of dihydroxyaromatic compound used in the reaction (including that which is part of the chainstopper itself).

Catalysis is normally achieved by the use of an aliphatic or heterocyclic tertiary amine that is soluble in the organic phase of the reaction mixture, such as those used to prepare the chainstopper. The catalyst is generally employed at a level of about 0.10 to about 5.0 mole percent, based on moles of total dihydroxyaromatic compound used. Furthermore, the volume ratio of aqueous to organic phase at the conclusion of the interfacial reaction is usually in the range of about 0.4:1.0 to about 2.0:1.0.

The pH of the reaction is maintained in the range of about 9 to 14, usually by the controlled addition of an alkali or alkaline earth metal base such as sodium hydroxide to the reaction mixture. Reaction temperatures in the range of about 15° C. to 50° C. are usually employed.

An exemplary interfacial reaction would include bisphenol A as the dihydroxyaromatic compound; triethylamine as the catalyst; and the oligomeric phenylcarbonate bisphenol A chloroformate chainstopper of this invention normally supplied in an organic solution. Other details of the interfacial process are well-known in the art. Typically, the initial formulation is based on components which are to comprise the final product. As an example, bisphenol A, the catalyst, and a portion of the solvent and water are added to a batch reactor vessel under agitation. Phosgene may then be bubbled into the reaction mixture while the pH is monitored and controlled. The remaining water and solvent may be metered into the vessel as needed. The chainstopper of the present invention may be added to the reaction mixture initially, or may be added in increments throughout the course of phosgenation.

Samples may be extracted throughout the reaction and analyzed by gel permeation chromatographic techniques to continually measure molecular weight.

Recovery of the polycarbonate product may be achieved by conventional techniques, such as precipitation by a non-solvent, evaporation of solvent, and/or filtration.

As mentioned above, polycarbonates may also be prepared from bischloroformate compositions, i.e., prereaction of a dihydroxyaromatic compound with phosgene to form a bischloroformate composition, followed by contact of the bischloroformate with an interfacial polycarbonate formation catalyst to form a linear aromatic polycarbonate. A non-limiting specific example of this process is provided in application Ser. No. 046,768, mentioned above. In brief, bischloroformate compositions are first prepared by known methods, e.g., the reaction of phosgene with a dihydroxyaromatic compound such as those discussed above. The aromatic bischloroformate composition may then be reacted with the chainstopper of the present invention in a reaction system which also contains water, a substantially inert, substantially water-insoluble organic liquid such as methylene chloride, and an alkali or alkaline earth metal base. The resulting product will be a partially capped bischloroformate composition in which the chainstopper performs the same function as the monohydroxyaromatic chainstopper of application Ser. No. 046,768.

As also described in application Ser. No. 046,768, formation of the partially capped bischloroformate composition may be effected under any interfacial reaction conditions suitable for the reaction of chloroformates with hydroxyaromatic compounds. For example, reaction temperatures may be in the range of about 0–50° C, while the pH of the aqueous phase in the reaction mixture may range from about 2 to about 11.5. The proportion of chainstopper to aromatic bischloroformate will depend on the desired molecular weight of the polycarbonate product, and can thus easily be determined without undue experimentation by those of ordinary skill. Chainstopper amounts of about 0.5–7.0 mole percent, based on structural units in the bischloroformate composition, are typical.

The partially capped bischloroformate composition may then be contacted with an interfacial polycarbonate formation catalyst and further aqueous alkali metal or alkaline earth metal base. This contact is generally effected in the presence of the organic liquid of the prior step. At this stage, additional dihydroxyaromatic compounds may be added to provide certain desired characteristics for the final product, as discussed above.

Examples of polycarbonate formation catalysts are given in Ser. No. 046,768 and in U.S. Pat. Nos. 4,217,438 and 4,368,315 both of which are incorporated by reference herein. These include the amines discussed earlier. Triethylamine is most preferred when viewed in terms of availability, cost, and effectiveness.

The polycarbonate formation reaction from bischloroformates may be conducted at a temperature in the range of about 0–100° C, and preferably at about 20–50° C; at a pH in excess of 10, preferably in the range of about 10.5–12.5; and using an amount of catalyst within the range of about 0.25–3.0 mole percent, based on structural units in the bischloroformate composition.

Formation of the polycarbonates may be carried out by batch techniques, as well as by the continuous techniques described above. The polycarbonate product may then be recovered by any of the above-mentioned procedures.

In conclusion, use of the chainstopper of the present invention results in highly improved polycarbonate preparation as carried out by a variety of techniques. In addition to accurate and effective molecular weight control, the formation of undesirable diarylcarbonate by-products is substantially eliminated. The examples which follow demonstrate some embodiments of the present invention, and are given by way of illustration and not by way of limitation. All parts are by weight, unless otherwise indicated.

EXAMPLE 1

This example describes the preparation of an oligomeric bisphenol A bischloroformate mixture, which is a precursor material to one of the chainstoppers of the present invention. A 1 liter, four neck, agitated flask was charged with bisphenol A (104 g, 0.456 moles), methylene chloride (50 mL), and water (40 mL). The mixture was phosgenated for 80 minutes at 2.2 grams/-minute while maintaining the pH at 3.5. After phosgenation was completed, the pH was maintained while the two-phase mixture was stirred for 20 minutes to hydrolyze residual phosgene. Methylene chloride (25 mL) and water (300 mL) were added to the reaction products and stirred, followed by separation of the aqueous phase. The methylene chloride solution of the oligomeric bisphenol A bischloroformate was then stored under 3N hydrochloric acid. Chromatograms of the product showed a mixture of oligomers with bisphenol A bischloroformate as the dominant component.

EXAMPLE 2

This example describes the preparation of an oligomeric phenylcarbonate bisphenol A chloroformate chain-stopper of the present invention.

An aliquot of the methylene chloride phase (315 mL) from Example 1, which contained 65.52 grams (0.287 moles) bisphenol A equivalent, was transferred to a 1 liter three neck agitated flask. A solution consisting of methylene chloride (SO mL), phenol (6.0 grams, 0.064 moles) and triethylamine (7.0 grams, 0.069 moles) was added to the flask dropwise. After addition was completed, the solution was stirred for an additional 15 minutes. A 3N hydrochloric acid solution (150 mL) was added to the reaction mixture to quench the reaction and extract the white triethylamine hydrochloride which had precipitated from the reaction.

Analysis showed less than 200 ppm phenol; a very minor amount of dimer; and a major amount of trimer or higher oligomers. Biscapped bisphenol A was below detection limits.

EXAMPLE 3

This example describes the preparation of an aromatic polycarbonate by the use of the chainstopper of the present invention. A 2 liter four neck agitated flask was charged with bisphenol A (53.48 grams, 0.235 moles), methylene chloride (375 mL), water (280 mL) and triethylamine (0.725 gram, 0.007 moles). The chainstopper was provided to the reaction mixture by adding an aliquot of the methylene chloride phase from Example 2 (either 50 mL or 20 mL - shown in Table 1), which contained the chainstopper. The reaction mixture was phosgenated for 13 minutes at 2.2 grams/minute while the pH was maintained at 10.5 by the addition of a 50% by weight sodium hydroxide solution. After phosgenation, the reaction was purged with nitrogen to remove residual phosgene. The methylene chloride phase was then washed twice with 3N hydrochloric acid (150 mL), and twice with water (150 mL). The water-washed methylene chloride phase was then passed through a bed of silica gel. The methylene chloride was removed by heating in an oven at 88° C, leaving the desired product. A control sample was generated by simply replacing the oligomeric chainstopper with phenol in this procedure. The pertinent results of these experiments are set out in Tables 1, 2 and 3. As is well-known in the art, intrinsic viscosity is an accurate indicator of polycarbonate molecular weight, and is therefore used as such for the sake of convenience.

TABLE 1

COMPARISON OF PHENOL CHAINSTOPPER WITH CHAINSTOPPER OF THE PRESENT INVENTION

| Chainstopper-type[a] | Level[b] (mole %) | Amount of Diphenylcarbonate Formation (ppm) | Intrinsic viscosity (dL/g) |
|---|---|---|---|
| Control (Phenol) | 3.3 | 1000 | 0.50 |
| Control (Phenol) | 4.5 | 1330 | 0.42 |
| Oligomeric Carbonate | 3.2 | 571 | 0.47 |
| Oligomeric Carbonate | 1.4 | 524 | 0.67 |

[a]Chainstoppers obtained from Example 2.

[b]Moles chainstopper per mole of bisphenol A employed, including that used in the chainstopper.

The data shown in Table 1 demonstrate that the oligomeric carbonate chainstoppers of the present invention are very effective in controlling the molecular weight of polycarbonates. Furthermore, their use results in a large decrease in the amount of diphenylcarbonate by-product.

The data in Tables 2 and 3 below were obtained by varying the amounts of control chainstopper and oligomeric carbonate chainstopper for a polycarbonate synthesis reaction identical to that described in Example 3.

TABLE 2

INTRINSIC VISCOSITY AS A FUNCTION OF CHAINSTOPPER LEVEL: CONTROL CHAINSTOPPER (PHENOL)

| Phenol (grams) | Intrinsic Viscosity (dL/g) |
|---|---|
| 0.193 | 0.62 |
| 0.228 | 0.57 |
| 0.274 | 0.61 |
| 0.319 | 0.48 |
| 0.365 | 0.45 |

TABLE 3

INTRINSIC VISCOSITY AS A FUNCTION OF CHAINSTOPPER LEVEL: OLIGOMERIC CARBONATE CHAINSTOPPER

| Oligomeric Carbonate (grams) | Intrinsic Viscosity (dL/g) |
|---|---|
| 6.36 | 0.99 |
| 9.54 | 0.82 |
| 12.72 | 0.66 |
| 19.08 | 0.47 |
| 22.26 | 0.50 |

The data shown above further demonstrate that very accurate control of molecular weight can be achieved by the use of the chainstopper of the present invention.

While the invention is described with respect to some of its embodiments, it will be apparent to those of ordinary skill in the art that certain modifications and changes may be made without departing from the broad teachings herein. It is thus intended that the foregoing disclosure be limited only by the claims appended hereto.

What is claimed is:

1. A chainstopper compound, for controlling the molecular weight of polycarbonates, having the formula

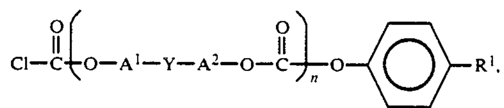

wherein each of $A^1$ and $A^2$ is a substituted or unsubstituted phenylene group, Y is a bridging group wherein one or two atoms separate $A^1$ from $A^2$, $R^1$ is hydrogen or a branched- or straight-chain alkyl group containing up to about 15 carbon atoms and n is an integer from 1 to about 10.

2. The chainstopper compound of claim 1 wherein $A^1$ and $A^2$ are each p-phenylene, and Y is isopropylidene.

3. The chainstopper compound of claim 2 wherein n is an integer from 1-5.

* * * * *